(12) United States Patent
Ju (10) Patent No.: US 11,490,921 B2
(45) Date of Patent: Nov. 8, 2022

(54) CLAMP FOR ATTACHING OR DETACHING MEDICAL SAVER

(71) Applicant: IMEDICOM CO., LTD., Gunpo-si (KR)

(72) Inventor: Don Soo Ju, Gunpo-si (KR)

(73) Assignee: IMEDICOM CO., LTD., Gunpo-si (KR)

( * ) Notice: Subject to any disclaimer, the term of this patent is extended or adjusted under 35 U.S.C. 154(b) by 50 days.

(21) Appl. No.: 17/258,300

(22) PCT Filed: Jul. 11, 2019

(86) PCT No.: PCT/KR2019/008535
§ 371 (c)(1),
(2) Date: Jan. 6, 2021

(87) PCT Pub. No.: WO2020/022672
PCT Pub. Date: Jan. 30, 2020

(65) Prior Publication Data
US 2021/0137550 A1     May 13, 2021

(30) Foreign Application Priority Data
Jul. 23, 2018 (KR) .................. 10-2018-0085375

(51) Int. Cl.
*A61B 17/3205* (2006.01)
*A61B 17/00* (2006.01)
*F16B 7/04* (2006.01)

(52) U.S. Cl.
CPC ........ *A61B 17/3205* (2013.01); *F16B 7/0413* (2013.01); *A61B 2017/00477* (2013.01); *A61B 2217/005* (2013.01)

(58) Field of Classification Search
CPC ............ A61B 17/06161; A61B 17/122; A61B 17/2833; A61B 17/29; A61B 17/3205;
(Continued)

(56) References Cited

U.S. PATENT DOCUMENTS 6,635,072 B1* 10/2003 Ramamurti ............... B25B 7/14
606/208
2005/0004590 A1* 1/2005 Waters ................ A61B 17/282
606/170
(Continued)

FOREIGN PATENT DOCUMENTS

KR     10-2015-0120199 A     10/2015

*Primary Examiner* — Darwin P Erezo
*Assistant Examiner* — Christian D Knauss
(74) *Attorney, Agent, or Firm* — Rabin & Berdo, P.C.

(57) ABSTRACT

The present disclosure provides a clamp for attaching or detaching a medical shaver, in which the clamp is provided for attaching and detaching a suction tube (30) detachably coupled to and rotated together with a shaft (20) rotated in a shaver body, and includes: a body; a detachment groove (120) formed in a direction perpendicular to a longitudinal direction on a front surface of the body; a detachment slit (125) formed in a direction perpendicular to the longitudinal direction on an upper surface of the body to communicate with the detachment groove; and an attachment groove (145) formed along the longitudinal direction at a center of a right side surface of the body.

4 Claims, 11 Drawing Sheets

(58) Field of Classification Search
CPC . A61B 17/3217; A61B 17/3468; A61B 90/57;
A61B 50/20; A61B 50/30; A61B
2017/2926; A61B 2017/2945; A61B
2017/22035; F16B 7/0413; F16B 7/04;
F16B 7/0406; F16G 11/08; F16G 11/09;
F16G 11/10
See application file for complete search history.

(56) References Cited

U.S. PATENT DOCUMENTS

2005/0182368 A1\* 8/2005 Gillis .................... A61M 25/02
128/DIG. 26
2009/0177196 A1\* 7/2009 Zlock ................. A61B 17/7083
606/53

\* cited by examiner

CLAMP FOR ATTACHING OR DETACHING MEDICAL SAVER

TECHNICAL FIELD

The present disclosure relates to a clamp for attaching or detaching a member for performing suctioning function to or from a medical shaver that is attached to and used on a medical handpiece or the like, and more specifically, to a clamp device technology according to which it is possible to apply different forces between when attaching the suctioning member and when detaching the same.

BACKGROUND ART

Various tools are attached to a front of a handpiece that includes a driving means provided therein, to be used as surgical instruments in the course of a medical procedure such as a surgery and the like so as to discharge tissue fragments, scraped tissues, or pus produced during the surgery to the outside. For example, in orthopedics, a suction tip is attached to the front and a saline solution supply tube is formed on one side, such that during a procedure such as a surgery, saline solution is sprayed onto an affected area for cleaning and securing visibility, while the sprayed saline solution and blood spilled during the procedure are suctioned and discharged.

The related technology includes a medical handpiece disclosed in Korean Patent Laid-Open No. 10-2015-0120199. However, the related technology has shortcomings. That is, the parts serving as suction part are integrally formed and it is inconvenient to attach and detach the parts.

Therefore, there is a need to improve a structure of the shaver that is attached to the handpiece or the like, to have a structure that is convenient to use, and there is also a need to devise a means for detaching the suction part of the shaver.

SUMMARY

Technical Problem

An object of the present disclosure is to improve a structure of a shaver that is attached to a handpiece, to thus provide a removable suction part and make it easier to attach and detach the suction part, and it is another object of the present disclosure to provide separate and convenient equipment with which it is possible to attach and detach the suction member hygienically, rather than holding the suction member of the shaver by the operator's hand to attach or detach the same.

Technical Solution

The present disclosure provides a clamp for attaching or detaching a medical shaver, in which the clamp is provided for attaching and detaching a suction tube 30 that is detachably coupled to and rotated together with a shaft 20 rotated in a shaver body, and includes: a body; a detachment groove 120 formed in a direction perpendicular to a longitudinal direction on a front surface of the body; a detachment slit 125 formed in a direction perpendicular to the longitudinal direction on an upper surface of the body to communicate with the detachment groove; and an attachment groove 145 formed along the longitudinal direction at a center of a right side surface of the body.

The body includes: a first body 110 having a rotation shaft 140; and a second body 130 rotatably coupled to the first body by the rotation shaft, and the attachment groove 145 is formed between the first and second bodies, such that a gap of the attachment groove is changed by a rotating operation of the second body.

An elastic spring 150 is further included, which is provided between the first and second bodies, and the elastic spring applies an elastic force to the body in a direction in which the gap of the attachment groove is widened, and a plurality of steps are formed on an inner side of the attachment groove such that an inner diameter of the attachment groove is reduced.

The detachment groove 120 is formed in the center of the body such that, with the suction tube being positioned in the slit 125 for the detachment of the suction tube 30, it is possible to grip both ends of the body by hand.

Advantageous Effects

By the above configuration, the present disclosure improves the structure of the shaver such that the suction tube is detachably attached to the shaft and a greater force is required for separating and detaching than for attaching, and as a result, the suction tube is prevented from being detached while the shaver is in rotating operation, and the procedure is performed more stably.

The present disclosure provides an advantageous effect of convenience of attachment and detachment as well as hygiene by enabling an operator to attach and detach the suction member of the shaver by utilizing simple equipment, rather than holding and detaching the suction member by hand.

DETAILED DESCRIPTION

Figure 1:
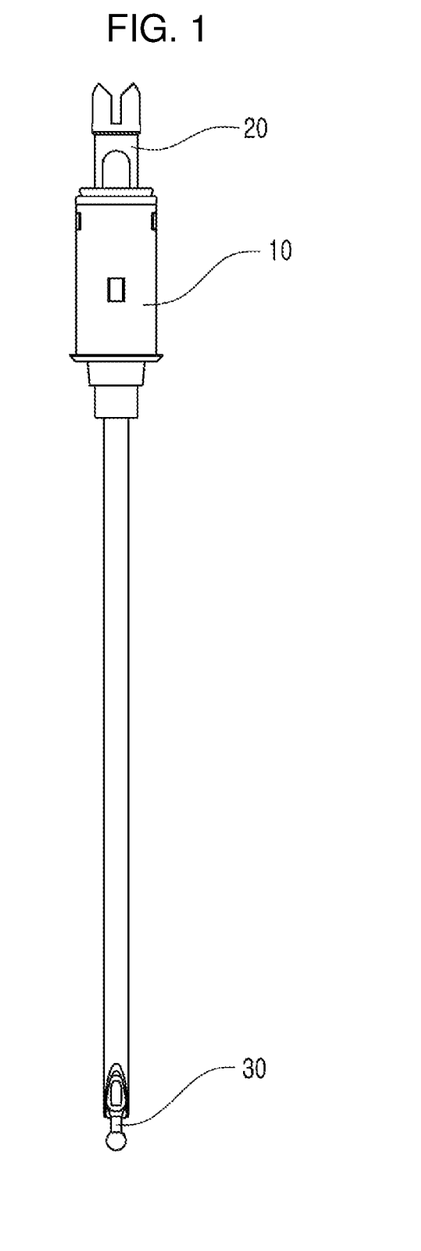
FIG. 1 illustrates a medical shaver according to an embodiment of the present disclosure.
Figure 2:
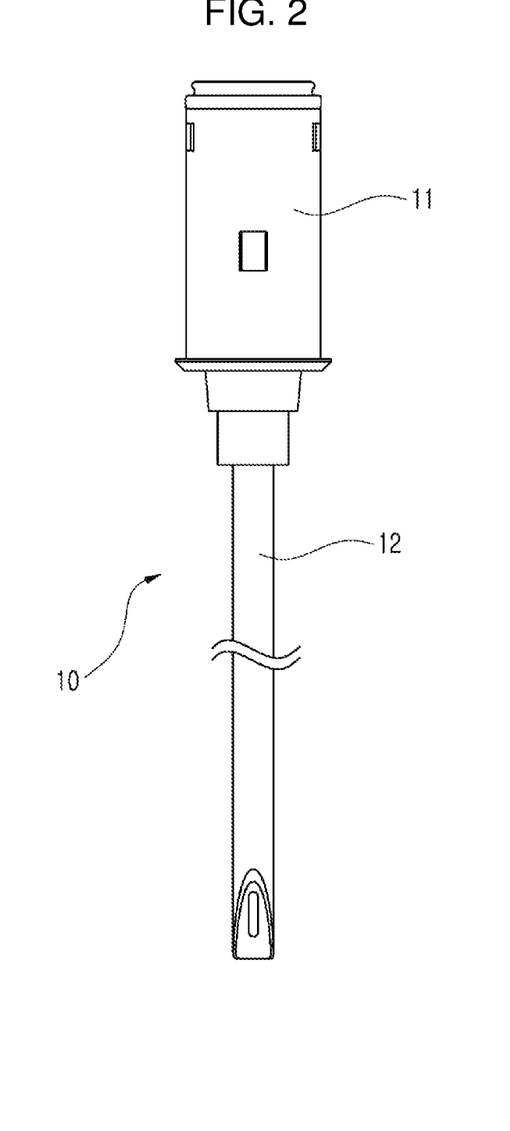
FIG. 2 illustrates only a shaver body and a shaft among the parts of the medical shaver according to an embodiment of the present disclosure.
Figure 3:
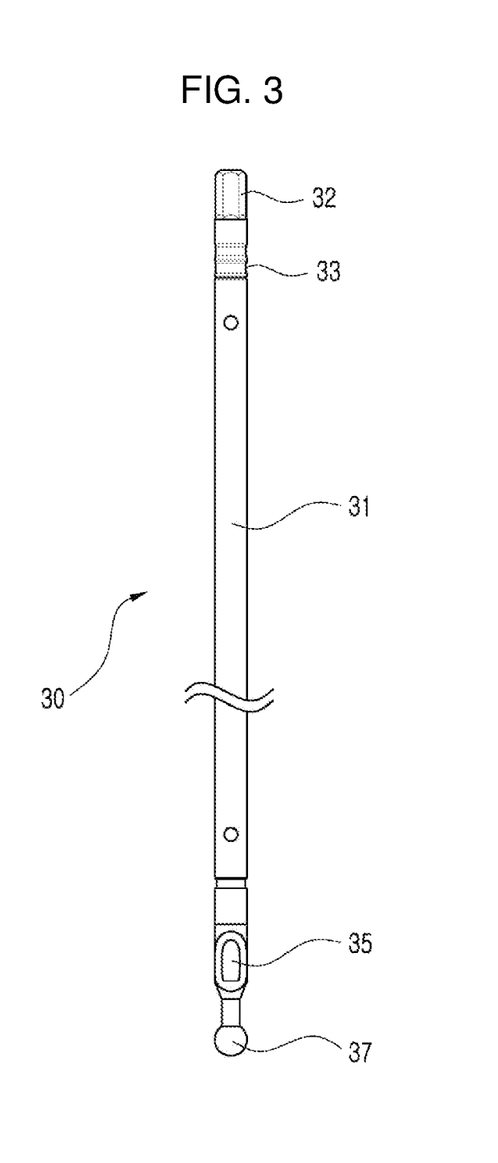
FIG. 3 is a cross-sectional view of FIG. 2.
Figure 4:
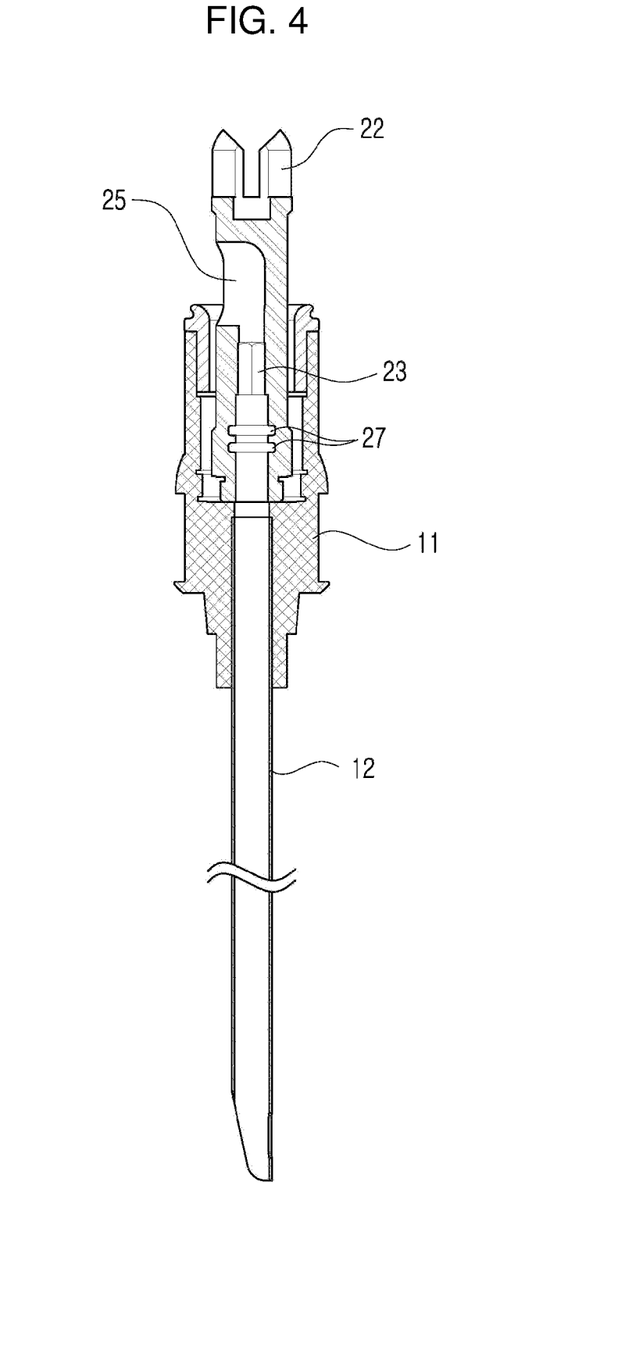
FIG. 4 illustrates a suction tube among the parts of the medical shaver according to an embodiment of the present disclosure.

FIG. 1 illustrates a medical shaver according to an embodiment of the present disclosure. FIG. 2 illustrates only a shaver body and a shaft, FIG. 3 is a cross-sectional view of FIG. 2, FIG. 4 illustrates a suction tube, and FIGS. 5 to 8 are cross-sectional views illustrating a process in which the suction tube and the shaft are coupled and separated in the medical shaver of the present disclosure.

According to the present disclosure, by referring to the drawings, the shaver of the present disclosure includes a shaver body 10 having a longitudinal hollow portion therein, and a shaft 20 and a suction tube 30 having one ends rotatably attached inside the shaver body. The shaft 20 and the suction tube 30, which are attached to the shaver body, are coupled to be rotated together. The shaver of the present disclosure is coupled to a rotation power generating device such as a medical handpiece (not shown), and has a motor coupling part 22 protruding from one side of a body 21 of the shaft 20 to be coupled to the rotation power generating device (motor, etc., not shown). As the shaft is rotated, the suction tube 30 coupled to the shaft is also rotated integrally.

The suction tube 30 has a shape of a tube having a hollow portion therein, and includes, formed at one end thereof, a docking part 32 coupled to a polygonal structure formed on an inner circumferential surface of the shaft. That is, the inner circumferential surface of the shaft has a polygonal (square, hexagonal) cross-sectional structure, and an outer circumferential surface of the docking part 32 has a corresponding polygonal structure, so that the docking part of the suction tube 30 is coupled to the shaft to be rotated integrally.

Figure 5:
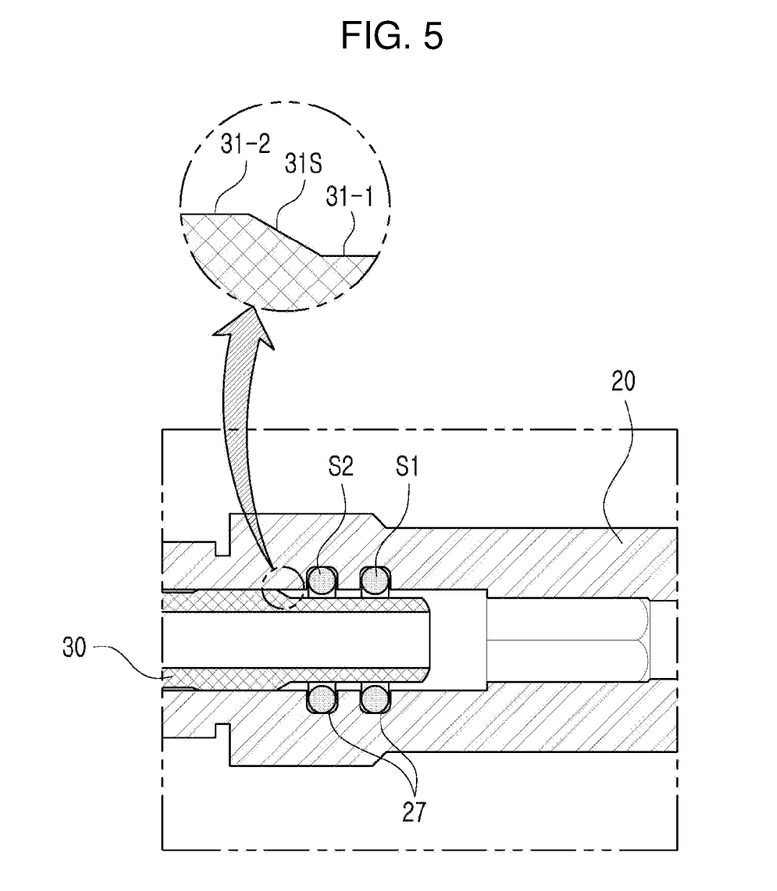
FIGS. 5 to 8 are cross-sectional views illustrating a process in which the suction tube and the shaft are coupled and separated in the medical shaver of the present disclosure.

When a portion of the suction tube that is coupled to the shaft is referred to as a coupling part, the coupling part has a first coupling part 31-1 formed at a rear end of the docking part and having a circular cross section, and a second coupling part 31-2 having a larger diameter than the first coupling part, having a second seating groove 33 formed on an outer circumferential surface, and having a circular cross section, and includes an inclined portion 31s formed between the first coupling part and the second coupling part (see FIG. 5).

In addition, the entire interior of the suction tube 30 has a hollow portion, and there is a suction hole 35 formed at one end of the hollow portion to serve as a suction port through which bone or tissue (hereinafter, discharged matter) is sucked and discharged to the outside as they are scraped during surgery. The discharged matter is sucked into the suction hole 35 and discharged into the hollow portion within the shaft through the hollow portion within the suction tube 30. In addition, the discharged matter is discharged to an external device (medical handpiece, and the like) through a discharge port 25 formed on one side of the shaft. The discharged matter is discharged by a vacuum pressure or the like acting on the discharge port as the shaft is rotated, which is the known technology commonly used in this field, and accordingly, a detailed description thereof will be omitted. The processing part 37 provided on a side of the suction hole of the suction tube is a part that performs an operation such as scraping tissues, or the like during surgery, and may have various shapes as cutting type.

Figure 9:
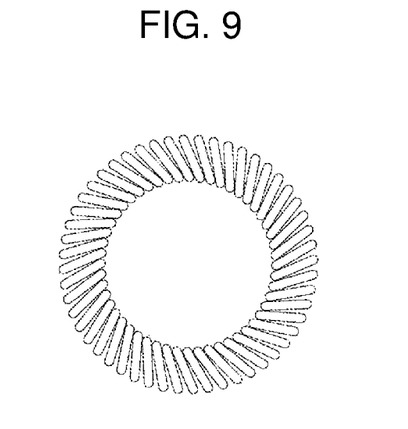
FIG. 9 illustrates a shape of a spring used in the medical shaver of the present disclosure.

Further, a first seating groove 27 for receiving a spring (s) seated therein is provided on the inner circumferential surface of the shaft, and a second seating groove 33 for receiving a spring (s) seated therein is provided on the outer circumferential surface of the suction tube. The spring (s) has a structure in which both ends of a coil spring are connected to form a ring shape as a whole (see FIG. 9), and the springs (s) are located in the first and second seating grooves and serve to couple the shaft and the suction tube to each other so that the shaft and the suction tube do not fall out from each other.

The present disclosure is designed such that, compared to a force required for attaching the suction tube to the shaft, a greater force is required for separating and detaching the same due to the structure of the springs (s) and the first and second seating grooves, and as a result, when the shaver is rotated, the separation of the suction tube is prevented and the procedure is performed more stably. Hereinafter, the process in which the suction tube and the shaft are coupled in the shaver and separated therefrom will be described with reference to the cross-sectional views shown in FIGS. 5 to 8.

The suction tube 30 has a coupling part to be coupled to the shaft, which includes a first coupling part 31-1 formed at a rear end of the docking part 32 and having a circular cross section, a second coupling part 31-2 having a larger diameter than that of the first coupling part, having a circular cross section, and having the second seating groove 33 formed on the outer circumferential surface, and an inclined portion 31s formed between the first coupling part and the second coupling part. Hereinafter, for convenience of explanation, it is assumed that there are two first seating grooves 27, two second seating grooves 33, and two springs (s) provided, respectively, although three or more of each may also be provided. Hereinafter, the springs are referred to as a first spring (s1) and a second spring (s2).

FIG. 5 shows a state in which the suction tube 30 is fitted in the hollow portion of the shaver body and coupled with the shaft 20, and the spring (s) is seated in the first seating groove 27 formed on the inner circumferential surface of the shaft 20, and in this case, the spring is in an extended state (non-compressed state) in the absence of separate force exerted thereon.

Figure 6:
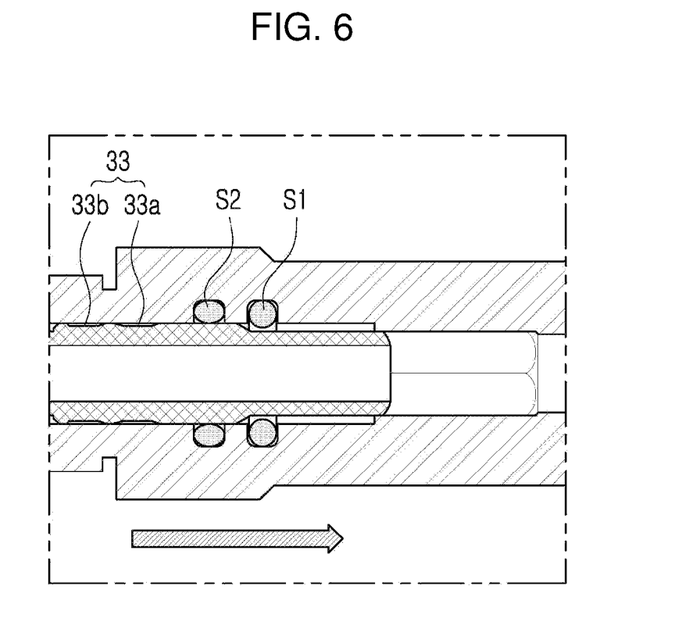

FIG. 6 shows a state in which the suction tube 30 is advanced for coupling, the second spring (s2) is located in the second coupling part 31-2 having a relatively large diameter, and the first spring (s1) is located in the first coupling part 31-1 having a relatively small diameter. That is, with the application of the coupling force, the second spring is moved along the inclined portion 31s into the compressed state, and the first spring is just before the compression.

Figure 7:
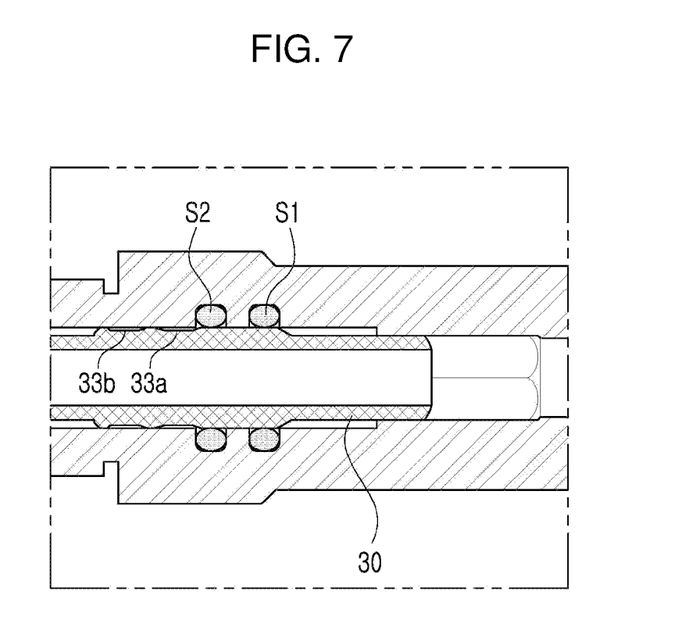
Figure 8:
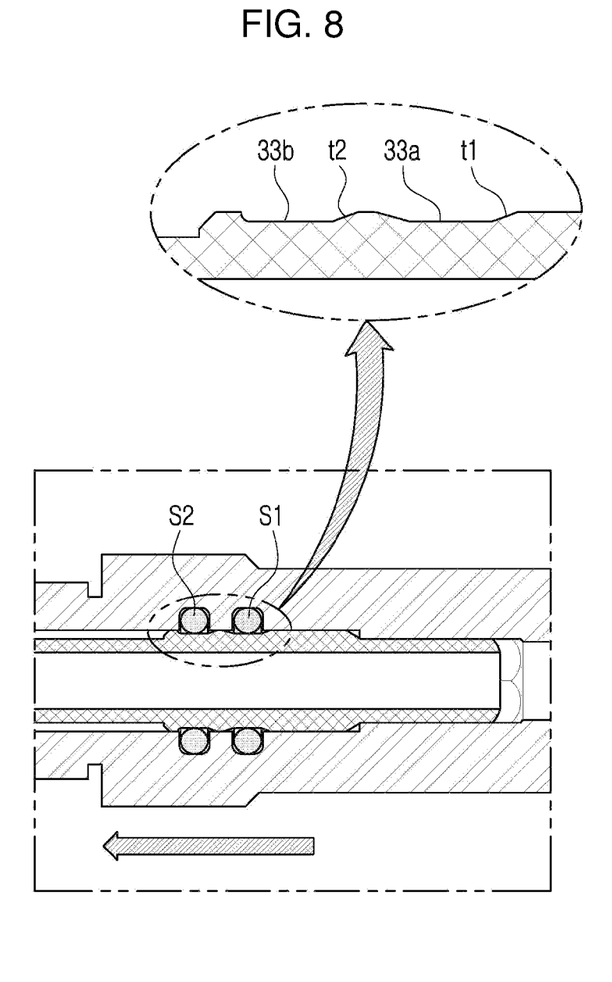

FIG. 7 shows a state in which both the first and second springs are compressed, the suction tube 30 is in the process of continuously advancing (to the right-hand side in the drawing) for coupling, and FIG. 8 shows a state in which the coupling of the suction tube 30 and the shaft 20 is completed, and each of the springs (s1, s2) is seated in the second seating groove 33 formed on the outer circumferential surface of the suction tube. There are two second seating grooves 33, as there are two springs 33a and 33b.

Through the process of FIGS. 5 to 8, the suction tube 30 and the shaft 20 are coupled. Meanwhile, the coupling in this coupling process requires the application of an external force in order to compress the spring when the spring (s) passes through the inclined portion 31s of the suction tube 30 (the friction force when sliding on the outer circumference of the suction tube in the compressed state is insignificant). However, referring to the coupling process, the two springs are compressed one by one, so the force required for compression is a relatively small force.

Consider the case where the suction tube 30 is separated from the shaft 20. In the coupled state shown in FIG. 8, the two springs (s1, s2) are seated in the second seating grooves 33a and 33b, respectively, at which state the springs are not compressed. In order to separate the suction tube 30, it is necessary to pull the suction tube 30 to the left-hand side in the drawing, and at this time, since the two springs (s1, s2) need to be compressed simultaneously to move over the steps (t1, and t2) of the second seating groove, the force required for detachment of the suction tube 30 is roughly about twice the force required for coupling.

Since the structure described above requires that both of the two special springs be contracted at the same time during detachment, it is required that a greater force is applied than the force that is required during coupling. That is, while the springs undergo compression deformation in turn in the process of attaching the suction tube to the shaft, the springs undergo deformation at the same time in the process of detaching the suction tube from the shaft, which means that the detaching force for detaching the suction tube from the shaft is greater than the attaching force for attaching the suction tube to the shaft In consideration of the fact that it takes a larger amount of force when separating (detaching) the parts of the shaver than when attaching the same, the present disclosure developed a clamp that enables both attaching and detaching movements of the parts of the shaver while considering the forces for the same.

Figure 10:
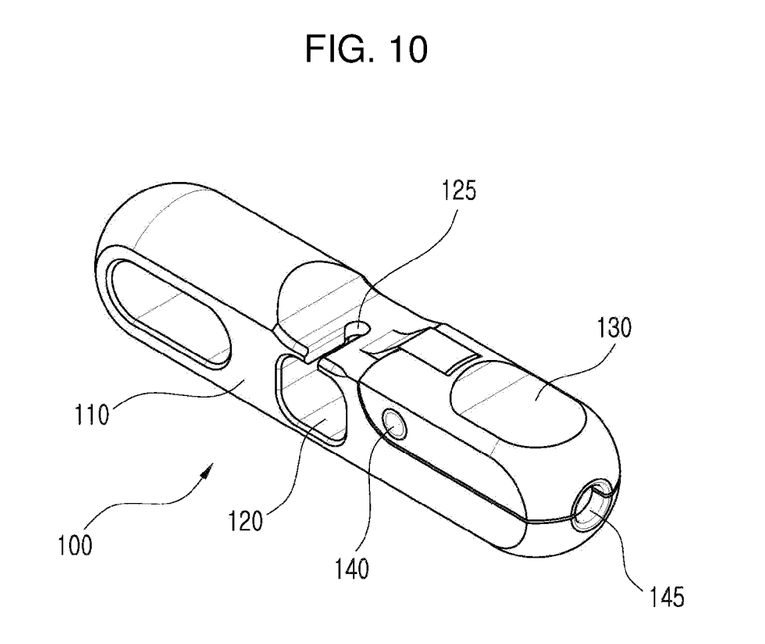
FIGS. 10 to 11 illustrate a clamp for attaching and detaching a medical shaver viewed from various angles according to an embodiment of the present disclosure.
Figure 11:
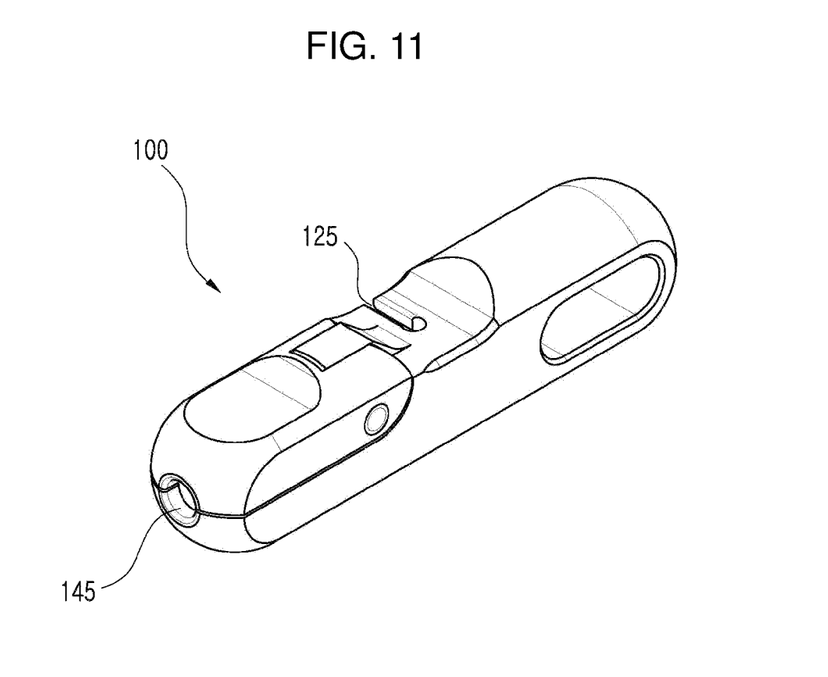
Figure 12:
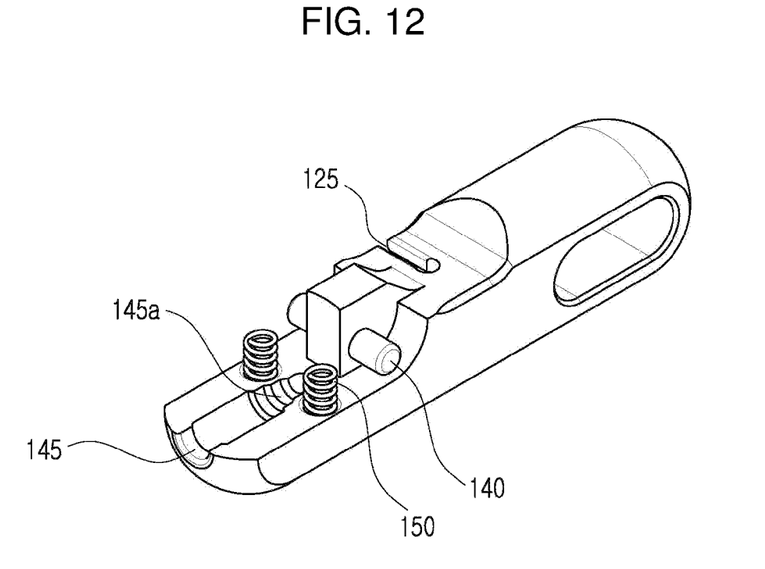
FIG. 12 illustrates the clamp for attaching and detaching a medical shaver from which certain parts are removed to expose the inside according to an embodiment of the present disclosure.
Figure 13:
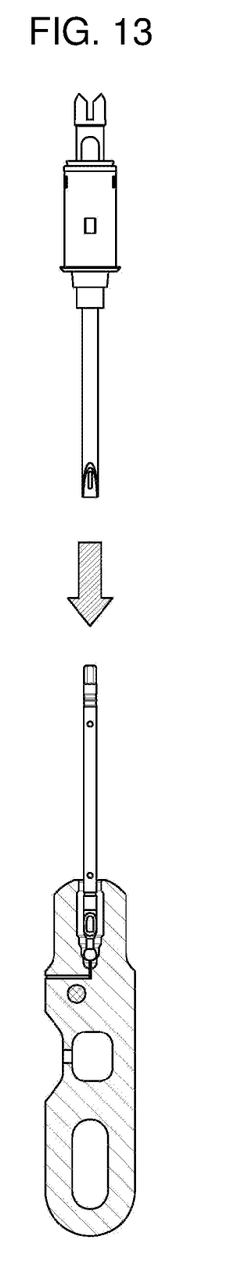
FIGS. 13 and 14 illustrate a clamp for attaching and detaching a medical shaver being used to attach or detach the parts of the shaver according to an embodiment of the present disclosure.
Figure 14:
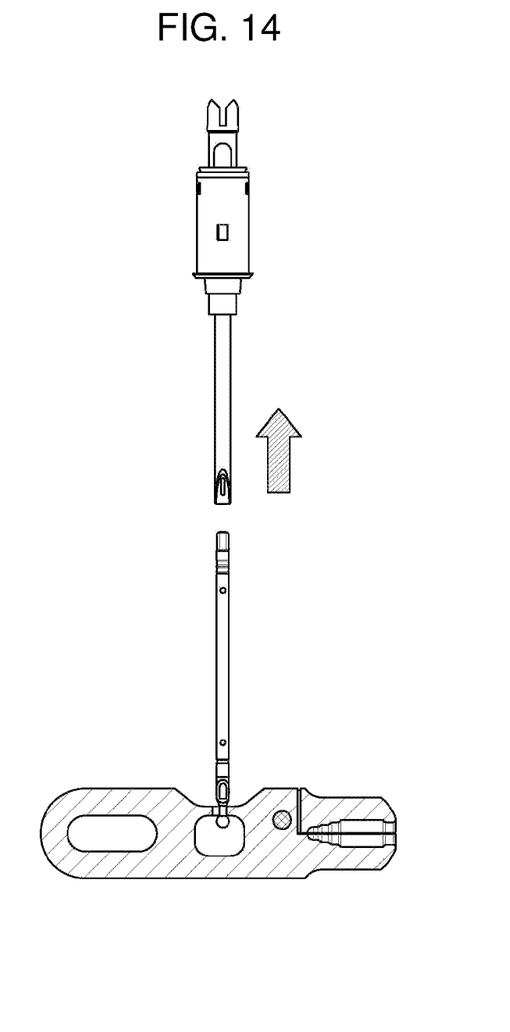

FIGS. 10 to 11 illustrate a clamp for attaching and detaching a medical shaver viewed from various angles according to an embodiment of the present disclosure, FIG. 12 illustrates the clamp for attaching and detaching a medical shaver from which certain parts are removed to expose the inside according to an embodiment of the present disclosure, and FIGS. 13 and 14 illustrate a clamp for attaching and detaching a medical shaver being used to attach or detach the parts of the shaver according to an embodiment of the present disclosure.

The clamp according to the present disclosure is a device provided for attaching and detaching the suction tube 30 that is detachably coupled to the shaft 20 rotated in a shaver body.

The clamp according to the present disclosure includes a body formed of a first body 110 and a second body 130. A rotation shaft 140 is attached inside the first body in a transverse direction (a direction perpendicular to the length direction of the body), and the second body 130 is coupled to the rotation shaft and rotatably coupled to the first body. An elastic spring 150 is provided between the first and second bodies, so that due to the pressure of the elastic spring pressing the second body, the elastic force is exerted on the body in a direction in which a gap between the bodies is widened.

An attachment groove 145 is formed between the first and second bodies to be used when attaching the suction tube 30 to the shaft 20. The attachment groove 145 is a groove formed from the center of the right side of the body toward the inside along the longitudinal direction as seen in FIG. 10, and because the attachment groove is formed between the first and second bodies, it receives the force of the elastic spring 150 and is always kept open. In order to attach the suction tube 30 to the shaft 20, the processing part 37 provided at the end of the suction tube 30 is placed in the attachment groove 145, and an operator secures the suction tube 30 while holding and pressing the first and second bodies by hand, and attaches it to the shaft 20 (see FIG. 13).

In addition, a plurality of steps are formed on an inner side of the attachment groove to reduce an inner diameter of the attachment groove, such that even when the diameter of the suction tube 30 or the size of the processing part 37 changes, they can still be used.

In addition, a detachment groove 120 is formed in a direction perpendicular to the longitudinal direction on a front surface of the body, and a detachment slit 125 is formed in a direction perpendicular to the longitudinal direction on an upper surface of the body to communicate with the detachment groove. To separate and detach the suction tube 30 from the shaft 20 by using this, the processing part 37 is inserted into the detachment groove 120, and the suction tube 30 is moved transversely to the inside of the body through the slit 125. Then, by pulling the shaver body 10 in the direction of separation, the suction tube 30 is separated from the shaft 20.

Because the detachment groove 120 is formed in the center of the body, when the suction tube is positioned in the slit 125 for the detachment of the suction tube 30, it is possible for the operator to grip both ends of the body by hand.

According to the present disclosure, even when a considerable force is required for detachment due to the configuration described above, the separation and detachment can be performed easily due to the slit structure, and it is also advantageous in terms of hygiene because it is not required to directly grip the suction tube 30 by hand for the detachment thereof.

What is claimed is:

1. A clamp for attaching or detaching a medical shaver, wherein the clamp is for attaching and detaching a suction tube that is detachably coupled to and rotated together with a shaft rotated in a shaver body, and comprises:
    a body including a first body having a rotation shaft and a second body rotatably coupled to the first body by the rotation shaft;
    a detachment groove formed in a direction perpendicular to a longitudinal direction on a front surface of the body;
    a detachment slit formed in a direction perpendicular to the longitudinal direction on an upper surface of the body to communicate with the detachment groove; and
    an attachment groove formed along the longitudinal direction at a center of one of lateral side surfaces of the body,
    wherein the attachment groove is formed between the first body and the second body such that a gap of the attachment groove is changed by a rotating operation of the second body.

2. The clamp of claim 1, further comprising an elastic spring provided between the first body and the second body,
    wherein the elastic spring applies an elastic force to the second body in a direction in which the gap of the attachment groove is widened.

3. The clamp of claim 2, wherein a plurality of steps are formed on an inner side of the attachment groove such that an inner diameter of the attachment groove is reduced.

4. The clamp of claim 1, wherein the detachment groove is formed in the center of the body such that, when the suction tube is positioned in the detachment slit for the detachment of the suction tube, it is possible to grip the lateral side surfaces of the body by hand.

* * * * *